(12) United States Patent
Hu (10) Patent No.: US 10,499,950 B2
(45) Date of Patent: Dec. 10, 2019

(54) LINE-SHAPED PAW-TYPE PATELLA EXTERNAL FIXATOR

(71) Applicant: Chengji Hu, Yueqing (CN)

(72) Inventor: Chengji Hu, Yueqing (CN)

( * ) Notice: Subject to any disclaimer, the term of this patent is extended or adjusted under 35 U.S.C. 154(b) by 101 days.

(21) Appl. No.: 15/796,754

(22) Filed: Oct. 28, 2017

(65) Prior Publication Data
US 2018/0042644 A1  Feb. 15, 2018

Related U.S. Application Data

(63) Continuation of application No. PCT/CN2016/000212, filed on Apr. 22, 2016.

(30) Foreign Application Priority Data

Apr. 29, 2015  (CN) .................... 2015 2 0282526 U (51) Int. Cl.
*A61B 17/64* (2006.01)
*A61B 17/60* (2006.01)
*A61B 17/66* (2006.01)

(52) U.S. Cl.
CPC .......... *A61B 17/6466* (2013.01); *A61B 17/60* (2013.01); *A61B 17/64* (2013.01); *A61B 17/66* (2013.01); *A61B 2017/603* (2013.01)

(58) Field of Classification Search
CPC ............................................. A61B 17/60–666
See application file for complete search history.

(56) References Cited

U.S. PATENT DOCUMENTS

| | | | | |
|---|---|---|---|---|
| 2,406,987 A | * | 9/1946 | Anderson | A61B 17/6441 606/59 |
| 4,365,624 A | * | 12/1982 | Jaquet | A61B 17/62 606/56 |
| 4,393,868 A | * | 7/1983 | Teague | A61B 17/6425 606/57 |
| 4,488,542 A | * | 12/1984 | Helland | A61B 17/6458 606/54 |
| 4,615,338 A | * | 10/1986 | Ilizarov | A61B 17/62 606/58 |
| 4,624,249 A | * | 11/1986 | Alvarez Cambras | A61B 17/6441 606/54 |
| 4,784,125 A | * | 11/1988 | Monticelli | A61B 17/62 606/56 |

(Continued)

*Primary Examiner* — Eduardo C Robert
*Assistant Examiner* — Michelle C Eckman
(74) *Attorney, Agent, or Firm* — Wayne & Ken, LLC; Tony Hom (57) ABSTRACT

The present invention provides two types of a line-shaped paw-type patella external fixator, comprising A type: two ends of a line-shaped main girder are respectively provided with pressure regulating fixing parts, an arc auxiliary girder is arranged below the line-shaped main girder, and two ends of the arc auxiliary girder are respectively provided with one auxiliary fastener and fixing needles; B type: one end of B type is the same with that of the A type, a b-shaped fixing part is provided below a q-shaped fixing part on the other end, a fixing needle is provided below the b-shaped fixing part, an auxiliary fastener is provided in the middle of the line-shaped main girder, and a splayed needle seat and an auxiliary fixing needle are arranged on both sides. The fixator has advantages of easy installation, wide adjustment range and minimal damage.

12 Claims, 12 Drawing Sheets

(56) References Cited

U.S. PATENT DOCUMENTS

| | | | | |
|---|---|---|---|---|
| 5,358,504 A * | 10/1994 | Paley | A61B 17/66 | 606/105 |
| 5,437,668 A * | 8/1995 | Aronson | A61B 17/62 | 606/54 |
| 5,681,309 A * | 10/1997 | Ross, Jr. | A61B 17/62 | 606/54 |
| 5,797,908 A * | 8/1998 | Meyers | A61B 17/6483 | 606/54 |
| 5,971,984 A * | 10/1999 | Taylor | A61B 17/62 | 128/898 |
| 6,129,727 A * | 10/2000 | Austin | A61B 17/62 | 606/56 |
| 6,355,037 B1 * | 3/2002 | Crosslin | A61B 17/6425 | 606/54 |
| 6,537,274 B1 * | 3/2003 | Katz | A61B 17/62 | 606/304 |
| 6,942,664 B1 * | 9/2005 | Voor | A61B 17/645 | 606/54 |
| 7,749,224 B2 * | 7/2010 | Cresina | A61B 17/6425 | 606/54 |
| 9,101,398 B2 * | 8/2015 | Singh | A61B 17/66 | |
| 9,408,635 B2 * | 8/2016 | Wong | A61B 17/6466 | |
| 9,872,706 B1 * | 1/2018 | Mullaney | A61B 17/6475 | |
| 9,931,137 B2 * | 4/2018 | Wong | A61B 17/62 | |
| 2001/0051806 A1 * | 12/2001 | Ballier | A61B 17/645 | 606/54 |
| 2003/0153910 A1 * | 8/2003 | Janowski | A61B 17/645 | 606/56 |
| 2004/0133200 A1 * | 7/2004 | Ruch | A61B 17/60 | 606/54 |
| 2006/0200127 A1 * | 9/2006 | Ismail | A61B 17/66 | 606/59 |
| 2008/0221571 A1 * | 9/2008 | Daluiski | A61B 17/6466 | 606/54 |
| 2009/0312757 A1 * | 12/2009 | Kehres | A61B 17/62 | 606/56 |
| 2010/0076435 A1 * | 3/2010 | Eslami | A61B 17/6475 | 606/59 |
| 2014/0031822 A1 * | 1/2014 | Venturini | A61B 17/64 | 606/59 |
| 2016/0030028 A1 * | 2/2016 | Van Dyke | A61B 17/025 | 606/90 |
| 2016/0038185 A1 * | 2/2016 | Disegi | A61B 17/6416 | 606/59 |
| 2017/0224383 A1 * | 8/2017 | Wong | A61B 17/6458 | |
| 2018/0243007 A1 * | 8/2018 | Jaramillo | A61B 17/62 | |
| 2018/0368888 A1 * | 12/2018 | Wigginton | A61B 17/6425 | |

* cited by examiner

LINE-SHAPED PAW-TYPE PATELLA EXTERNAL FIXATOR

FIELD OF THE INVENTION

The present invention relates to a line-shaped paw-type patella external fixator, and the fixator is mainly used for external fixing human knee joint patella fracture or comminuted fracture.

BACKGROUND OF THE INVENTION

At present, a variety of fixing methods are commonly used in patella fracture in the medical field, and the most common is tension band internal fixation, that is: 1. fixing with steel wire for operation, 2. wearing steel needle and winding steel wire etc. These operations are traumatic and the healing process delays the exercise timing of the joint function, patella is increased and incomplete knee joint adhesion appeared, and the most intuitive disadvantage is patients need to suffer from a second operation; 3. some of the existing external fixators are cumbersome in installation, limited in fixing adjustable range, and joint function exercise is obstructed by the fixator, and some of the existing external fixations are rarely promoted by the medical community due to big traumas; 4. traditional Chinese medicine conservative treatment method uses external fixation binding, and the advantage is no wound; however, the disadvantage is that bone integration is hard to be completed, stability is poor, and it is difficult to be protected. The exercise timing of the joint function is delayed, resulting in enlarged and deformed patella, which can affect the function quality of joints and even occur more serious consequences, such as oppressive ulcer.

SUMMARY OF THE INVENTION

In order to solve the technical problem, the present invention provides a line-shaped paw-type patella external fixator. According to the present invention, doctors can install the fixator in advance according to the displacement of patella fracture of patients, and invasive surgery is not required for not particularly serious comminuted patella fractures. The installed fixing needle can be placed into the best position of the patella and fix directly, which has advantages of simple operation, adjustable and stable position, early exercising of knee joint function, and the patients do not suffer from the second operation, and it is a new technique for the treatment of patella minimally invasive surgery in orthopedics.

For this purpose, the present invention provides a line-shaped paw-type patella external fixator, and two common types are designed to treat different patella fracture and match different patella fracture displacement: paw type and hand type, the paw-type patella external fixator has four fixing points like the eagle paw and is minimally invasive and sturdy; the hand-type patella external fixator has five fixing points like the five fingers and is sensitive and stable. A is the paw-type patella external fixator comprising a line-shaped main girder, pressure regulating fasteners are respectively provided on both ends of the line-shaped main girder, a pressure regulating nut is provided on one end of the line-shaped main girder and can rotatably adjust fastening on screw threads on the line-shaped main girder, an arc auxiliary girder is provided below the line-shaped main girder, an auxiliary fastener and a fixing needle are respectively provided on both ends of the arc auxiliary girder, and an auxiliary fastener is provided on the middle section of the line-shaped main girder, wherein the middle section of the line-shaped main girder (1) can be further provided with an auxiliary fastener.

B. The hand-type patella external fixator comprises a line-shaped main girder, a pressure regulating fastener is provided on one end of the line-shaped main girder, an arc auxiliary girder is provided below the line-shaped main girder, an auxiliary fastener and a fixing needle are respectively provided on both ends of the arc auxiliary girder; a q-shaped fixing part is provided on the other end of the line-shaped main girder, and a b-shaped fixing part is provided below the q-shaped fixing part; an auxiliary fastener is provided on the middle section of the line-shaped main girder, a splayed needle seat and an auxiliary fixing needle are provided on both ends of the auxiliary fastener.

The present invention provides a paw-type patella external fixator, comprising A type: pressure regulating fasteners are respectively provided on both ends of the line-shaped main girder. Two types are designed for convenient installation and option demand, the pressure regulating fastener is pushed by the pressure regulating nut to adjust in the best place and fixing, an arc auxiliary girder is provided below the pressure regulating fastener, and an arc auxiliary girder is provided with a calibration fixing hole in the middle for fixing hole. The arc auxiliary girder can be placed asymmetrically by moving left or right according to the need if patella displacement is special, auxiliary fasteners are provided on both ends of the arc auxiliary girder. The patella external fixator can be adjusted laterally by moving the auxiliary fastener, and can be adjusted the slop by rotating the auxiliary fastener, the design of multi-directional adjustment can match different patella fracture displacement, needle holes are provided below the auxiliary fastener. After the fixing needle is inserted into the needle hole, the fixing needle is adjusted to the best position by the reinforcing nut, and is fixed by the fastening screw.

Figure 7:
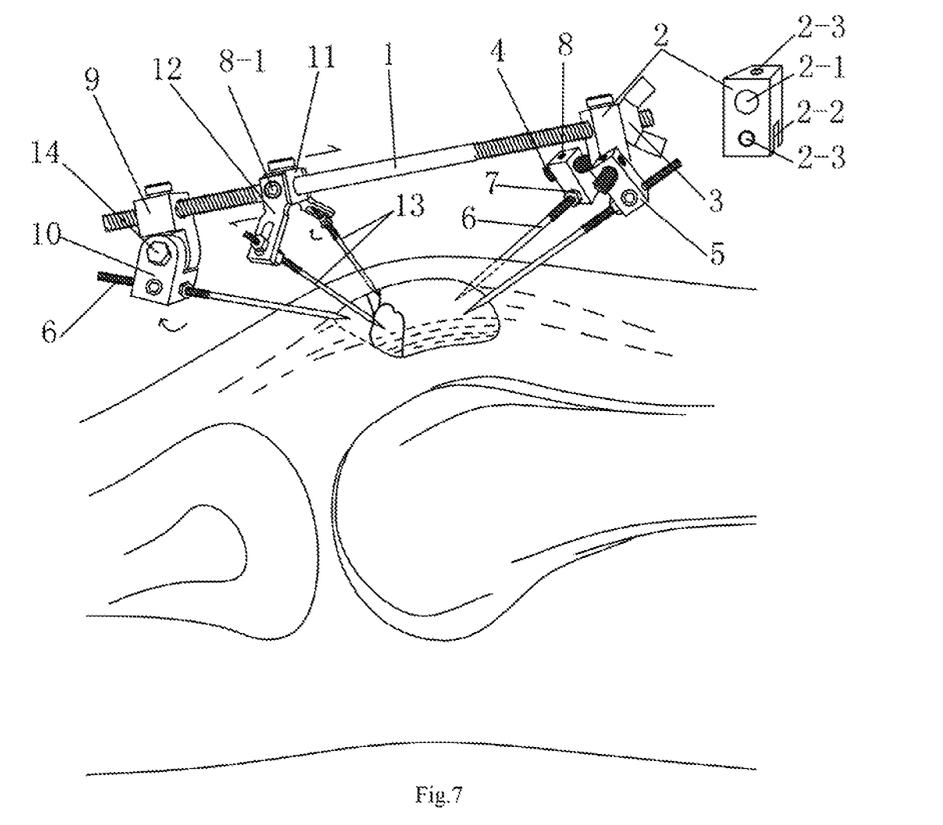
FIG. 7 is a side view of a line-shaped paw-type patella external fixator (B type) of the present invention fixed on the skeleton.
Figure 8:
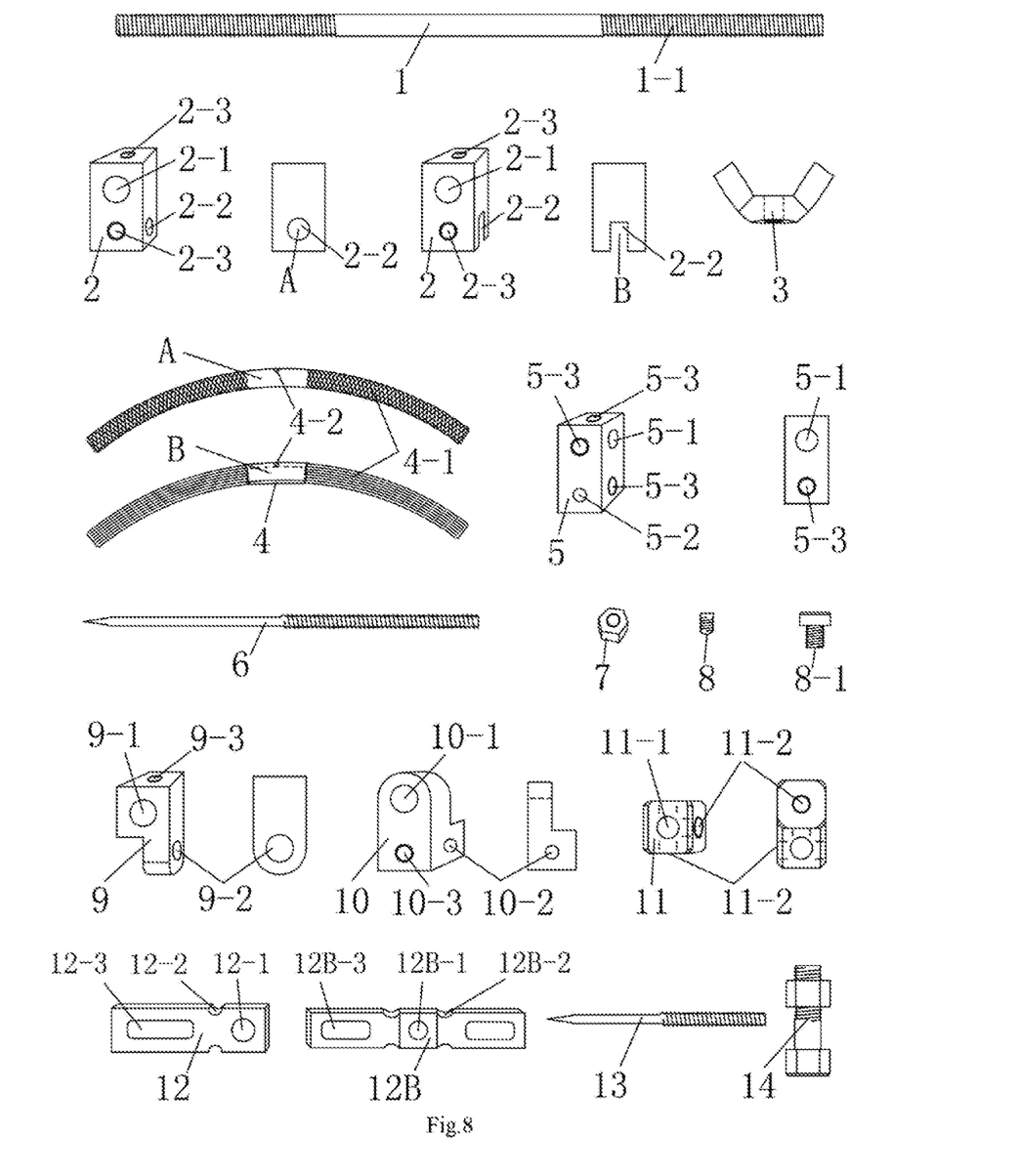
FIG. 8 is parts of A type and B type of the present invention.
Figure 9:
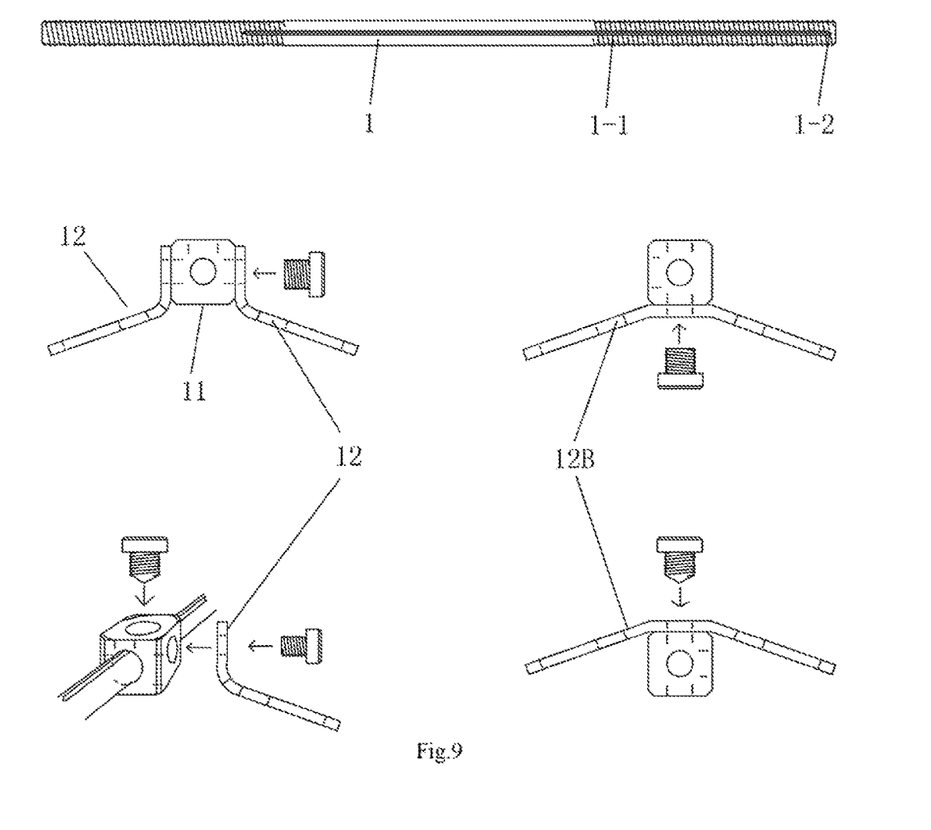
FIG. 9 is a structural schematic view between the auxiliary fastener, two types of the splayed needle seat and the line-shaped main girder of the present invention (B type).

B type: a pressure regulating fastener is provided on one end of the line-shaped main girder, and a q-shaped fixing part is provided on the other end of the line-shaped main girder; the pressure regulating fastener is adjusted to the best position by the pressure regulating nut. The design below the pressure regulating fastener is the same as the A type; a b-shaped fixing part is provided below the q-shaped fixing part on the other end of the line-shaped main girder. The b-shaped fixing part is designed as single needle hole. To solve the need for different positions of the patella fracture displacement to advance the minimal design of the area, the adjustment slope can be rotated, after the fixing needle is inserted into the needle hole, the fixing needle is adjusted to the best position by the reinforcing nut and is fixed by the fastening screw; the design of the auxiliary fastener is for matching of the splayed needle seat, and it can be placed asymmetrically by moving front or back according to patella fracture in different position; the splayed needle seat is designed into two types: the design of A type can be rotated to adjust the angle of the auxiliary fixing needle, the design of the small half circle in the middle is easy to be bended and adjust the angle, the design of the oval-shaped needle hole allows the needle to move left and right and is beneficial for space adjustment of the auxiliary fixing needle, after the auxiliary fixing needle is inserted into the needle hole, the auxiliary fixing needle is adjusted to the best position by the reinforcing nut (as shown in FIG. 7); the design of B type can adjust in tandem (as shown in FIG. 9). Special explanation: 1. the auxiliary fastener, two kinds of splayed needle seat and the auxiliary fixing needle belong to auxiliary fixing, the auxiliary fixing can be used or not used for A type and B type based on displacement of patella fracture. 2. there are two types of arc auxiliary girder and the pressure regulating fastener, the arc auxiliary girder and the pressure regulating fastener of A type can be exchanged with those of B type as needed.

In the figures, 1—line-shaped main girder, (1-1)—screw threads, (1-2)—concave rail groove; 31—auxiliary fixing kit; 2—pressure regulating fixing part, (2-1)—main girder hole, (2-2)—auxiliary girder hole, (2-3)—screw hole; 3—pressure regulating nut, 4—arc auxiliary girder, (4-1)—skidproof stripe, (4-2)—calibration fixing hole; 5—auxiliary fastener, (5-1)—auxiliary girder hole, (5-2)—needle hole, (5-3)—screw hole; 6—fixing needle; 7—reinforcing nut; 8—fastening screw, (8-1)—grub screw; 9—q-shaped fixing part, (9-1)—second main girder hole, (9-2)—fixing hole, (9-3)—screw hole; 10—b-shaped fixing part, (10-1)—second fixing hole, (10-2)—second needle hole, (10-3)—screw hole; 11—auxiliary fastener, (11-1)—third main girder hole, (11-2)—screw hole; 12—splayed needle seat, (12-1)—third fixing hole, (12-2)—small half circle, (12-3)—oval-shaped needle hole, 12B—integrated splayed needle seat, (12B-1)—forth fixing hole, (12B-2)—small half circle, (12B-3)—oval-shaped needle hole; 13—auxiliary fixing needle; 14—screw kit.

DETAILED DESCRIPTION OF THE INVENTION

Figure 1:
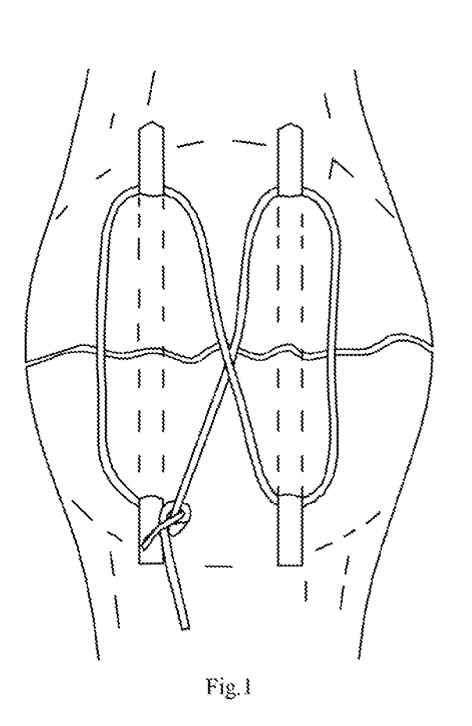
FIG. 1 and FIG. 2 are schematic views of internal fixation with tension band of traditional surgery for patella fracture.
Figure 2:
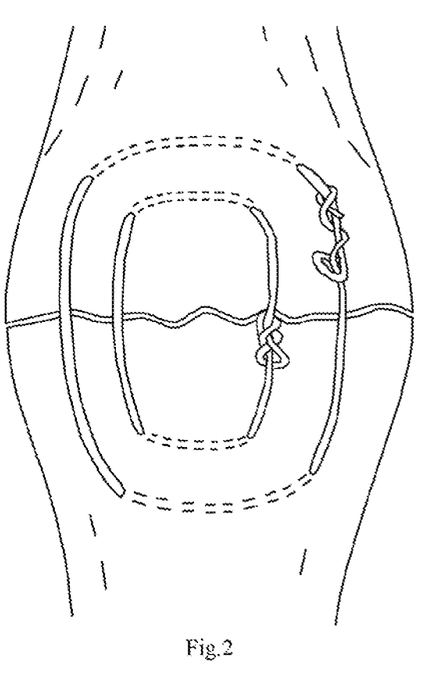
Figure 3:
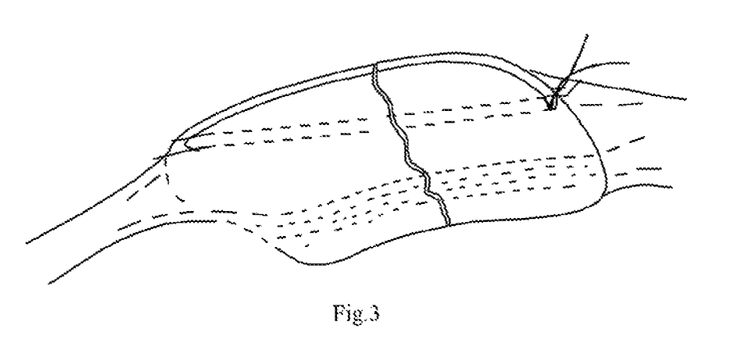
FIG. 3 is a side view of FIG. 1 and FIG. 2.

As shown in FIG. 1 and FIG. 2, the disadvantages of the traditional surgical methods for patella fracture are that: 1. a big opening is needed to expose the entire articular surface, and the surrounding tissue of the patella is destroyed. The body patella and the surrounding tissue are equally important according to theoretical analysis, however, traditional operation destroy the outer tissue to repair the patella, which is like natural and man-made disasters. If the operation is successful, the patients need to suffer from the second operation to take out the fixture; 2. if the operation is not ideal, the cut is badly damaged, the joint function exercise time is delayed, and functional disorders of the knee joint occur, the consequences are very serious.

Figure 6:
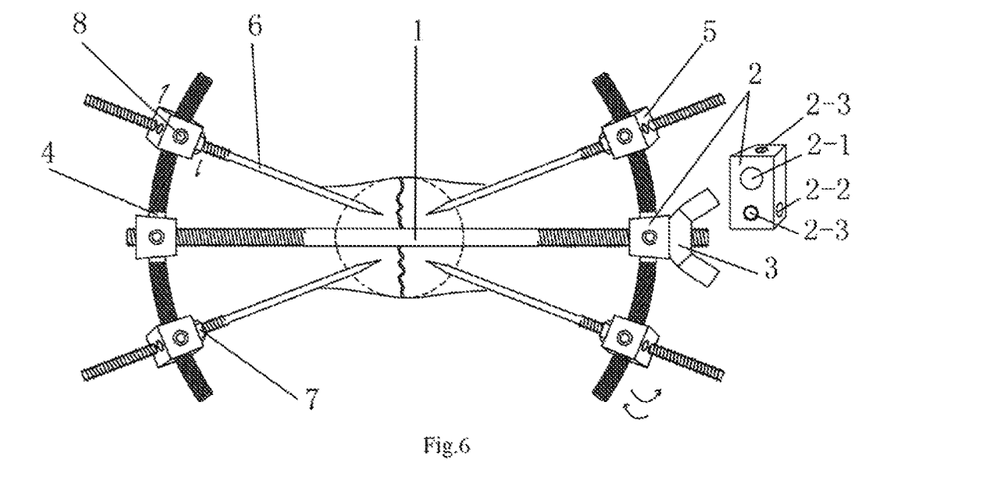
FIG. 6 is a structural plan view of an embodiment of a line-shaped paw-type patella external fixator (A type) of the present invention.

As shown in FIG. 6, a line-shaped paw-type patella external fixator comprises a line-shaped main girder (1), a pressure regulating fastener (2), a pressure regulating nut (3), an arc type auxiliary girder (4), an auxiliary fastener (5), fixing needles (6), a reinforcing nut (7) and a fastening screw (8). The line-shaped main girder (1) is a girder structure with a circular cross section; both ends of the line-shaped main girder (1) are respectively provided with screw threads (1-1), and both ends of the line-shaped main girder (1) are respectively provided with the pressure regulating fastener (2). The pressure regulating nut (3) is arranged on one end of the line-shaped main girder (1) a main girder hole (2-1) is provided on an upper end of the pressure regulating fastener (2), and an auxiliary girder hole (2-2) and a screw hole (2-3) are provided on a lower end of the pressure regulating fastener (2). The pressure regulating fastener (2) is connected to the line-shaped main girder (1) through the main girder hole (2-1) and the screw threads (1-1); the arc type auxiliary girder (4) is provided in the auxiliary girder hole (2-2), and the fastening screws (8) are provided in the screw hole (2-3). The arc auxiliary girder (4) has a circular cross section, skidproof stripes (4-1) are provided respectively at both ends of the arc auxiliary girder (4), a calibration fixing hole (4-2) is provided in the middle of the arc auxiliary girder (4), the auxiliary fasteners (5) are provided respectively at both ends of the arc auxiliary girder (4), and four auxiliary fasteners (5) are respectively arranged at both ends of the arc type auxiliary girder (4). The number of the fixing needle 6 is four, fixing needles 6 are averagely provided on each auxiliary fastener (5). The auxiliary fastener (5) is rectangular, an auxiliary girder hole (5-1) is provided on an upper end of the auxiliary fastener (5), a needle hole (5-2) and a screw hole (5-3) are provided on a lower end of the auxiliary fastener (5); the auxiliary girder hole (5-1) is mounted on the arc auxiliary girder (4), and the fixing needle (6) is provided in the needle hole (5-2), a screw thread of the fixing needle (6) is mounted on the reinforcing nut (7), and the fastening screw (8) is provided in the screw hole (5-3).

As shown in FIG. 7, a line-shaped paw-type patella external fixator comprises a line-shaped main girder (1), a pressure regulating fastener (2), a pressure regulating nut (3), arc type auxiliary girder (4), auxiliary fasteners (5), a fixing needle (6), a reinforcing nut (7), a fastening screw (8), a grub screw (8-1), a q-shaped fixing part (9), a b-shaped fixing part (10), an auxiliary fastener (11), a splayed needle seat (12), auxiliary fixing needles (13) and a screw kit (14). The line-shaped main girder (1) has a circular cross section, both ends of the line-shaped main girder (1) are respectively provided with screw threads (1-1), concave rail slots (1-2) are respectively provided on both ends of the line-shaped main girder (1), the pressure regulating fastener (2) and the pressure regulating nut (3) are provided on one end of the line-shaped main girder (1). The q-shaped fixing part (9) is provided on the other end of the line-shaped main girder (1), the auxiliary fastener (11) is provided in the middle section of the line-shaped main girder (1), a main girder hole (2-1) is provided on an upper end of the pressure regulating fastener (2), and an auxiliary girder hole (2-2) and a screw hole (2-3) are provided on a lower end of the pressure regulating fastener (2), the pressure regulating fastener (2) is connected to the line-shaped main girder (1) by the main girder hole (2-1) and the screw threads (1-1), the fastening screw (8) is provided in the screw hole (2-3), the pressure regulating nut (3) is provided next to the adjustment fastening (2). The arc auxiliary girder (4) is provided in an auxiliary girder groove (2-2) of the pressure regulating fastener (2), the arc auxiliary girder (4) has a circular cross section, skidproof stripes (4-1) are provided respectively on two ends of the arc auxiliary girder (4), a calibration fixing hole (4-2) is provided in the middle of the arc auxiliary girder (4). The auxiliary fastener (5) is provided respectively on two ends of the arc auxiliary girder (4), and two auxiliary fasteners (5) are provided respectively on two ends of the arc type auxiliary girder (4); the auxiliary fastener (5) is rectangular, an auxiliary girder hole (5-1) is provided on an upper end of the auxiliary fastener (5), a needle hole (5-2) and a screw hole (5-3) are provided on a lower end of the auxiliary fastener (5), the auxiliary girder hole (5-1) is mounted on the arc auxiliary girder (4), and the fixing needle (6) is provided in the needle hole (5-2), screw threads of the fixing needle (6) is mounted on the reinforcing nut (7), and the fastening screw (8) is provided in the screw hole (5-3); the q-shaped fixing part (9) is provided on the other end of the line-shaped main girder (1), and an upper end of the q-shaped fixing part (9) is square shape, and is provided with a second main girder hole (9-1), and a lower end of the q-shaped fixing part (9) is half-cube with a lower rounded shape and is provided with a fixing hole (9-2), a screw hole (9-3) is provided on a top end of the q-shaped fixing part (9), the q-shaped fixing part (9) is connected to the line-shaped main girder (1) by the second main girder hole (9-1) and the screw threads (1-1), the fastening screws (8) are provided in the screw hole (9-3), an upper end of the q-shaped fixing part (10) is half-cube with an upper rounded shape, and is provided with a second fixing hole (10-1), a needle hole (10-2) and a screw hole (10-3) are provided on the rectangular in a lower end, the fixing hole (9-2) of the q-shaped fixing part (9) is connected to the second fixing hole (10-1), the screw kit (14) is provided in the fixing hole (9-2) and the second fixing hole (10-1), the fixing needle (6) is provided in the second needle hole (10-2), the reinforcing nut (7) is provided on the fixing needle (6), the fastening screws (8) are respectively provided in the screw hole (10-3); a third main girder hole (11-1) is provided on the auxiliary fastener (11), screw holes (11-2) are provided on both sides and top of the auxiliary fastener (11); each of the splayed needle seat (12) is rectangular bended, a third fixing hole (12-1) is provided on tan upper end of the splayed needle seat (12), a semicircle slot (12-2) is provided on an upper middle of the splayed needle seat (12), an oval-shaped needle hole (12-3) is provided on a lower end of the splayed needle seat (12), screw holes (11-2) are connected with third fixing holes (12-1) by grub screws (8-1), the auxiliary fixing needle (13) is provided in the oval-shaped needle hole (12-3), reinforcing nuts (7) are provided on the screw threads of the auxiliary fixing needle (13), and reinforcing nuts (7) are fixed up and down to the oval-shaped needle hole.

Embodiment 1

Figure 4:
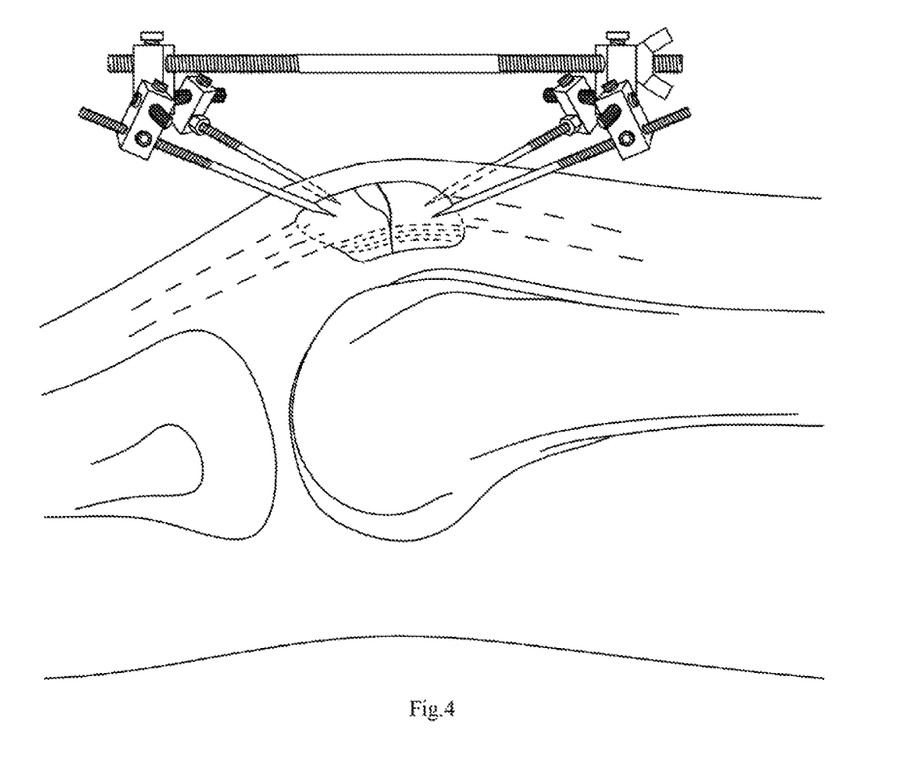
FIG. 4 is a side view of a line-shaped paw-type patella external fixator (A type) fixed on the skeleton.
Figure 5:
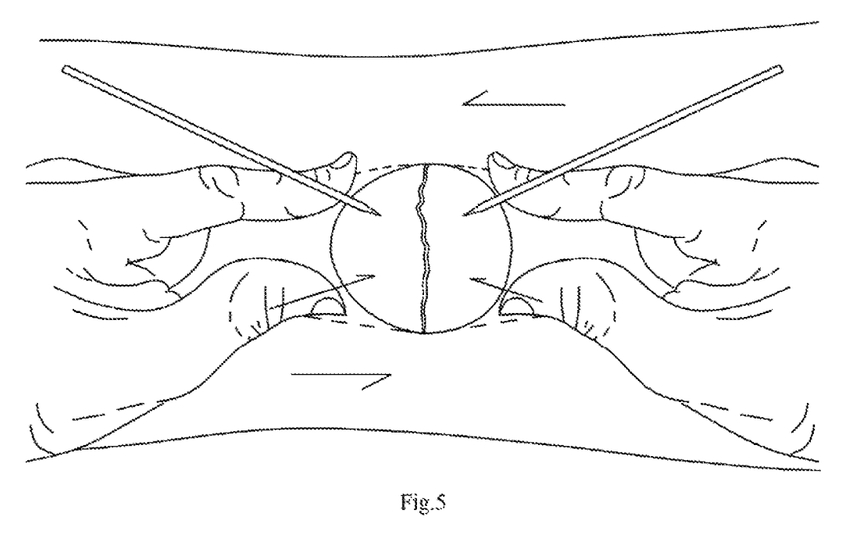
FIG. 5 is a schematic view of external fixing patella fracture of the injured with two thumbs and two forefingers of a doctor.

As shown in FIG. 4 and FIG. 5, A type of the present invention is the method for external fixing patella fracture with the line-shaped paw-type patella external fixator comprising: 1) swelling without surgery, first installing the fixator according to the displacement of X-ray patellar fracture based on figures, 2) disinfecting, 3) injecting local anesthetics, 4) external fixing the patella with the doctor's two thumbs and two forefingers (see FIG. 5), two hands push up and down heavily until a patellar shape is protruded, 5) then putting the ready external fixator in the four fingers, and selecting the best fixing point (it works better under X-ray), 6) loosening the fastening screw 8, 7) fixing four fixing needles 6 directly through the cortex into the patella continuously (see FIG. 5 and FIG. 6), 8) reversing the reinforcing nut 7 previously installed on the screw threads of a lower end of the fixing needle 6 and pressurizing the fixing needle 6 to determine the position of the fixing needle 6 is suitable, and 9) twisting the fastening screw 8; and then checking whether it needs to be adjusted, moving the auxiliary fastener 5 to adjust horizontally, turning the auxiliary fastener 5 to adjust slope, twisting or reversing the pressure regulating nut 3 to adjust the pressure regulating fastener 2 on the main girder 1 to the best position and fix, and tightening all the fastening screws 8 to fix.

Embodiment 2

As shown in FIG. 7, B type of the present invention is the method for external fixing patella fracture with the line-shaped paw-type patella external fixator, comprising: 1) swelling without surgery, installing the fixator according to the displacement of X-ray patella fracture based on the figure, 2) disinfecting, 3) injecting local anesthetics, 4) external fixing the patella with the doctor's two thumbs and two forefingers (see FIG. 5), two hands push up and down heavily until a patellar shape is protruded, 5) selecting the best position of the lower end of the patella (it works better under X-ray), fixing one fixing needle 6 into the center point between the quadriceps and the patella against the patella, then adding two more fixing needles on the patella, 6) installing the fixator front and back (see FIG. 7), 7) reversing the reinforcing nut 7 previously installed on the screw threads of a lower end of the fixing needle 6 and pressurizing the fixing needle 6 to determine the position of the fixing needle 6 is suitable, and 8) twisting the fastening screw 8; if patella is comminuted fracture and needs auxiliary fixing, following steps are taken: loosening the auxiliary fastener fastening screw 8, moving to the best position and fixing, 2) putting the auxiliary fixing needle 13 into the the oval-shaped needle hole, sleeving the reinforcing nut 7 on lower screw threads of the auxiliary fixing needle 13, selecting the fixed point, 3) fixing two auxiliary fixing needles 13 into the patella, then reversing the reinforcing nut 7 and pressurizing the auxiliary fixing needle 13, and determining the appropriate position of the auxiliary fixing needle 13, and 4) fitting the oval-shaped needle hole, fixing with the reinforcing nut 7 above the oval-shaped needle hole. Then checking whether it needs to be adjusted, moving the auxiliary fastener 5 to adjust horizontally, turning the auxiliary fastener 5 to adjust slope, moving the auxiliary fastener and adjusting front and back, rotating the splayed needle seat to adjust the angle, rotating the b-shaped fixing part to adjust the slope, twisting or reversing the pressure regulating nut 3 to adjust the pressure regulating fastener 2 on the main girder 1 to the best position and fix, and tightening all the fastening screws 8 or 8-1 and fixing.

Embodiment 3

The method for external fixing patella fracture with the line-shaped paw-type patella external fixator comprises: 1) performing a surgery, doctors take different measures according to the different conditions of patella fracture of the injured. For those requiring surgery, matched fixator is selected and fixed according to the displacement of patella fracture of the injured. A type: 1) selecting the best fixed point, 2) loosening the fastening screw 8 on the fixing needle 6, 3) fixing the fixing needle 6 into the patella directly (see FIG. 4 or 6), 4) reversing the reinforcing nut 7 so as to pressurize the fixing needle 6 and determining the appropriate position, 5) tightening all the fastening screws 8; then checking whether it needs to be adjusted, moving the auxiliary fastener 5 to adjust horizontally, turning the auxiliary fastener 5 to adjust slope, twisting or reversing the pressure regulating nut 3 to adjust the pressure regulating fastener 2 on the main girder 1 to the best position and fix, and tightening all the fastening screws 8 or 8-1 and fixing.

Embodiment 4

Figure 10:
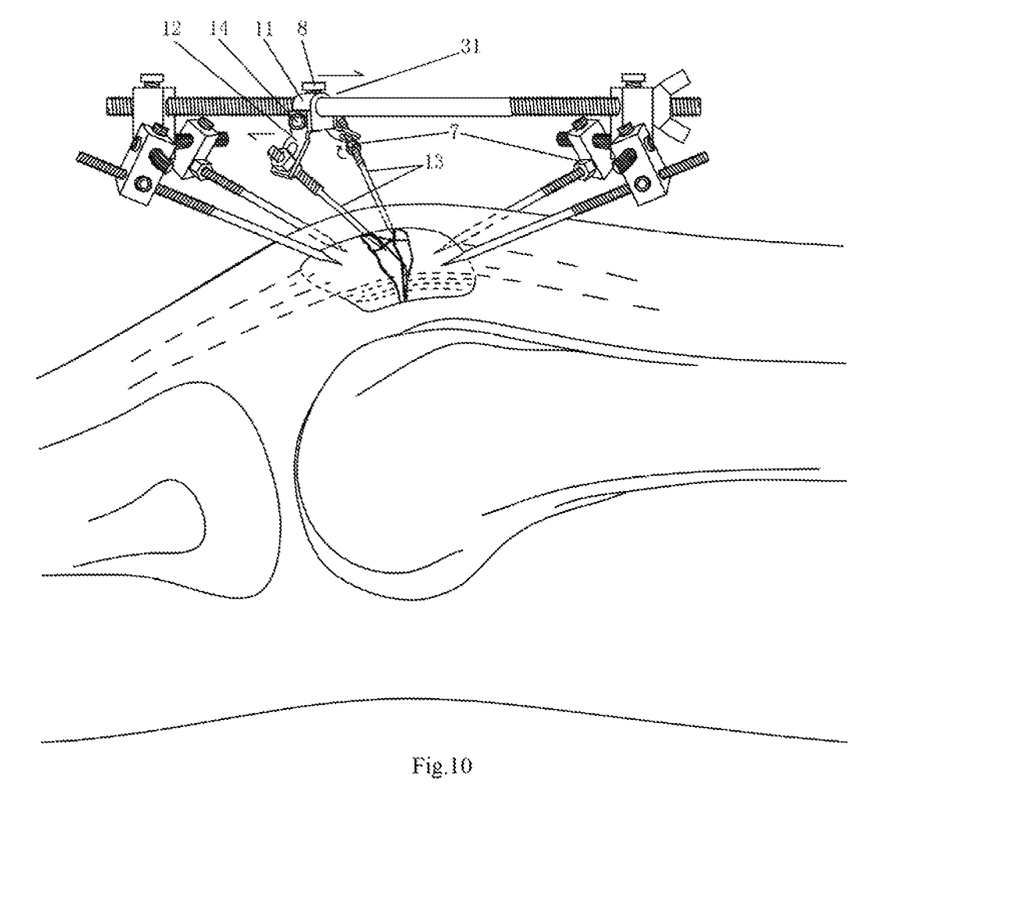
FIG. 10 is a structural view of embodiment 4 of the present invention.
Figure 11:
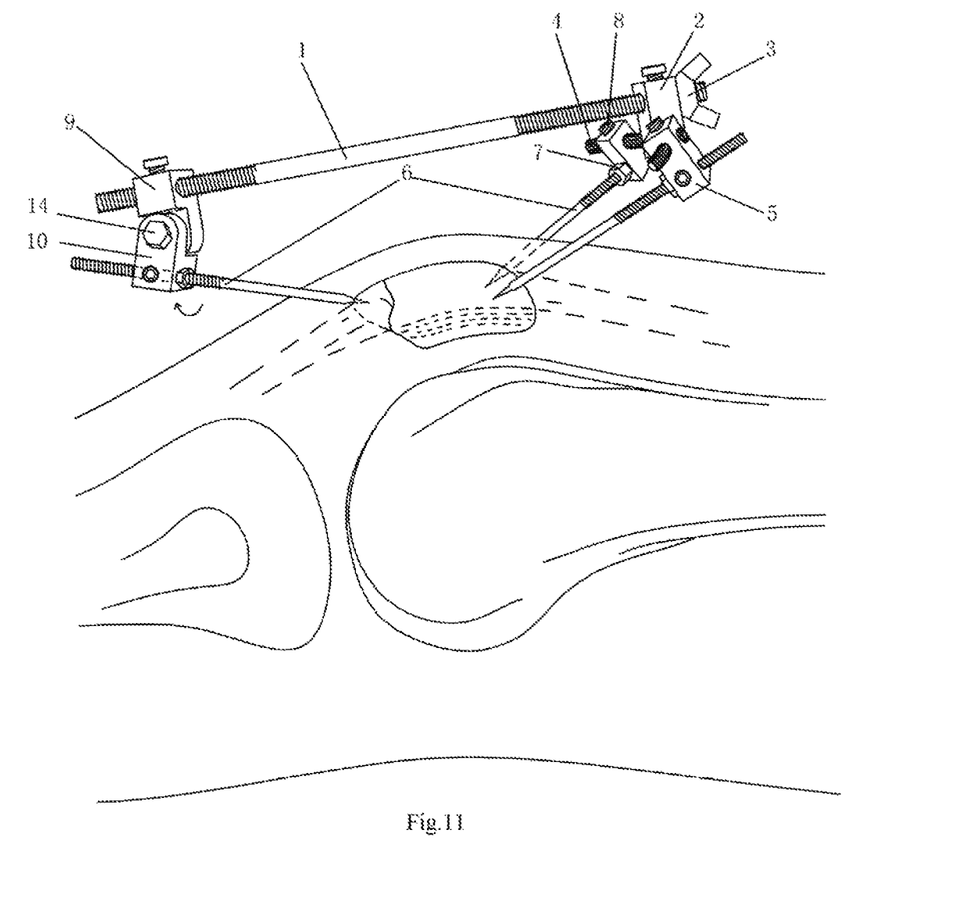
FIG. 11 is an effect view of the present invention without auxiliary fasteners (B type).
Figure 12:
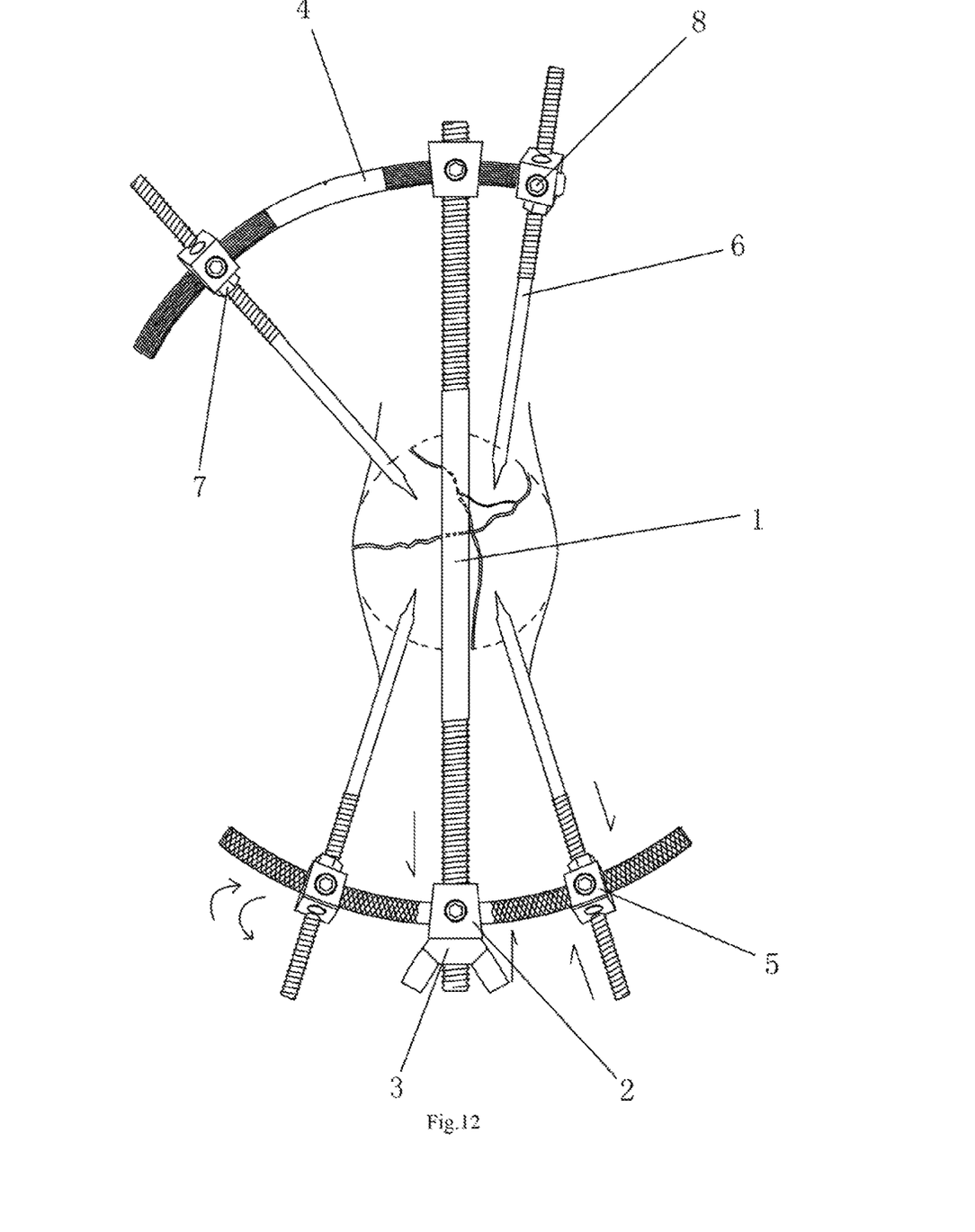
FIG. 12 is an asymmetrical setting effect view of the present invention (A type).

As shown in FIG. 10, the embodiment is improved on the basis of the embodiment 1 according to of the different conditions of patella fracture of the injured. The auxiliary fixing kit 31 is provided in the middle of the line-shaped main girder 1, the auxiliary fixing kit 31 comprises an auxiliary fastener 11, a splayed needle seat 12 and an auxiliary fixing needle 13 arranged below the auxiliary fastener 11, the auxiliary fixing needle (13) is provided in a needle hole (12-3) of the splayed needle seat (12). The auxiliary fastener 11, the splayed needle seat 12 and the auxiliary fixing needle 13 are the same with the above embodiments and are not repeated herein.

What is claimed is:

1. A line-shaped paw-type patella external fixator, comprising:
    a line-shaped main girder (1), pressure regulating fasteners (2), a pressure regulating nut (3), an arc type auxiliary girder (4), auxiliary fasteners (5), fixing needles (6), a reinforcing nut (7) and fastening screws (8);
    wherein the line-shaped main girder (1) is a girder structure with a circular cross section; both ends of the line-shaped main girder (1) are respectively provided with screw threads (1-1), and both ends of the line-shaped main girder (1) are respectively provided with the pressure regulating fasteners (2); the pressure regulating nut (3) is arranged on one end of the line-shaped main girder (1) and is rotatable on the screw threads (1-1) to adjust fastening; the arc type auxiliary girder (4) is provided below one of the pressure regulating fasteners (2); both ends of the arc type auxiliary girder (4) are respectively provided with the auxiliary fasteners (5), and the fixing needles (6) are provided below the auxiliary fasteners (5); the fastening screws (8) are respectively provided in a screw hole (2-3) of the pressure regulating fasteners (2) and a screw hole (5-3) of the auxiliary fasteners (5); the fixing needles (6) located below both ends of the line-shaped main girder (1) respectively hold against a cracked patella and secure the cracked patella.

2. The line-shaped paw-type patella external fixator according to claim 1, wherein a main girder hole (2-1) is provided on an upper end of the pressure regulating fasteners (2), and an auxiliary girder hole (2-2) and a screw hole (2-3) are provided on a lower end of the pressure regulating fasteners (2); the pressure regulating fasteners (2) are connected to the line-shaped main girder (1) through the main girder hole (2-1) and the screw threads (1-1); the arc type auxiliary girder (4) is provided in the auxiliary girder hole (2-2), and the fastening screws (8) are provided in the screw hole (2-3).

3. The line-shaped paw-type patella external fixator according to claim 1, wherein the arc auxiliary girder (4) has a circular cross section; skidproof stripes (4-1) are provided respectively at both ends of the arc auxiliary girder (4); a calibration fixing hole (4-2) is provided in the middle of the arc auxiliary girder (4); and the auxiliary fastener (5) is provided respectively at both ends of the arc auxiliary girder (4).

4. The line-shaped paw-type patella external fixator according to claim 1, wherein each of the auxiliary fasteners (5) is rectangular; an auxiliary girder hole (5-1) is provided on an upper end of the auxiliary fasteners (5), a needle hole (5-2) and a screw hole (5-3) are provided on a lower end of each of the auxiliary fasteners (5); the auxiliary girder holes (5-1) are mounted on the arc auxiliary girder (4), and the fixing needles (6) are provided in the needle holes (5-2), the reinforcing nut (7) is provided on screw threads of one of the fixing needles (6), and the fastening screws (8) are respectively provided in the screw holes (5-3).

5. The line-shaped paw-type patella external fixator according to claim 1, wherein the middle section of the line-shaped main girder (1) is further provided with an auxiliary fixing kit (31); the auxiliary fixing kit (31) comprises an auxiliary fastener (11), and a splayed needle seat (12) and an auxiliary fixing needle (13) arranged below both sides of the auxiliary fastener (11), the auxiliary fixing needle (13) is provided in a needle hole (12-3) of the splayed needle seat (12).

6. A line-shaped paw-type patella external fixator, comprising:
    a line-shaped main girder (1), a pressure regulating fastener (2), a pressure regulating nut (3), arc type auxiliary girder (4), first and second auxiliary fasteners (5), fixing needles (6), reinforcing nuts (7), fastening screws (8), a grub screw (8-1), a q-shaped fixing part (9), a b-shaped fixing part (10), a third auxiliary fastener (11), a splayed needle seat (12), auxiliary fixing needles (13) and a nut and bolt (14);
    the line-shaped main girder (1) has a circular cross section, both ends of the line-shaped main girder (1) are respectively provided with screw threads (1-1), and concave rail slots (1-2) are respectively provided on both ends of the line-shaped main girder (1); the pressure regulating fastener (2) and the pressure regulating nut (3) are provided on one end of the line-shaped main girder (1), the arc auxiliary girder (4) is provided in an auxiliary girder groove (2-2) of the pressure regulating fastener (2), the first and second auxiliary fasteners (5) are provided on both ends of the arc auxiliary girder (4), the fixing needles (6) are provided in a needle hole (5-2) in each of the first and second auxiliary fasteners (5); the q-shaped fixing part (9) is provided on the other end of the line-shaped main girder (1), and the b-shaped fixing part (10) is provided below the q-shaped fixing part (9), the fixing needles (6) are provided in a second needle hole (10-2) of the b-shaped fixing part (10); the third auxiliary fastener (11) is provided in the middle section of the line-shaped main girder (1), splayed needle seats (12) are arranged on both sides of the third auxiliary fastener (11), the auxiliary fixing needles (13) are provided in oval-shaped needle holes (12-3), the reinforcing nuts (7) are fixed on screw threads of the auxiliary fixing needles (13), the fixing needles (6) located below both ends of the line-shaped main girder (1) and the auxiliary fixing needles (13) hold against a cracked patella and secure the cracked patella.

7. The line-shaped paw-type patella external fixator according to claim 6, wherein a main girder hole (2-1) is provided on an upper end of the pressure regulating fastener (2), and an auxiliary girder hole (2-2) and a screw hole (2-3) are provided on a lower end of the pressure regulating fastener (2), the pressure regulating fastener (2) is connected to the line-shaped main girder (1) by the main girder hole (2-1) and the screw threads (1-1), the pressure regulating nut (3) is provided next to the pressure regulating fastener (2), the arc auxiliary girder (4) is provided in the auxiliary girder hole (2-2), and the fastening screws (8) are provided in the screw hole (2-3).

8. The line-shaped paw-type patella external fixator according to claim 6, wherein the arc auxiliary girder (4) has a circular cross section, skidproof stripes (4-1) are provided respectively on both ends of the arc auxiliary girder (4), a calibration fixing hole (4-2) is provided in the middle of the arc auxiliary girder (4), and four auxiliary fasteners (5) are provided respectively on both ends of the arc type auxiliary girder (4).

9. The line-shaped paw-type patella external fixator according to claim 6, wherein each of the first and second auxiliary fasteners (5) is rectangular, an auxiliary girder hole (5-1) is provided on an upper end of each of the first and second auxiliary fasteners (5), a needle hole (5-2) and a screw hole (5-3) are provided on a lower end of each of the first and second auxiliary fasteners (5), the auxiliary girder hole (5-1) is mounted on the arc auxiliary girder (4), and the fixing needles (6) are provided in the needle hole (5-2), screw threads of the fixing needles (6) are mounted on the reinforcing nut (7), and the fastening screws (8) are provided in the screw hole (5-3).

10. The line-shaped paw-type patella external fixator according to claim 6, wherein the q-shaped fixing part (9) is provided on the other end of the line-shaped main girder (1); an upper end of the q-shaped fixing part (9) is square shape and is provided with a second main girder hole (9-1), and a lower end of the q-shaped fixing part (9) is half-cube with a lower rounded shape and is provided with a fixing hole (9-2); a screw hole (9-3) is provided on a top end of the q-shaped fixing part (9), the b-shaped fixing part (10) is provided below the q-shaped fixing part (9); an upper end of the q-shaped fixing part (10) is half-cube with an upper rounded shape, and is provided with a second fixing hole (10-1), and a needle hole (10-2) and a screw hole (10-3) are provided on the rectangular in a lower end; the q-shaped fixing part (9) is connected to the line-shaped main girder (1) by the second main girder hole (9-1) and the screw threads (1-1), the fixing hole (9-2) of the q-shaped fixing part (9) is connected to the second fixing hole (10-1) by the nut and bolt (14), the fixing needle (6) is provided in the second needle hole (10-2) of the b-shaped fixing part (10), and the fastening screws (8) are respectively provided in the screw hole (9-3) of the q-shaped fixing part (9) and the screw hole (10-3) of the b-shaped fixing part (10).

11. The line-shaped paw-type patella external fixator according to claim 6, wherein the third auxiliary fastener (11) is provided on the middle section of the line-shaped main girder (1), a third main girder hole (11-1) is provided on the third auxiliary fastener (11), screw holes (11-2) are provided on both sides and top of the third auxiliary fastener (11), the fixing screws (8) are provided in the screw hole (11-2) on the top of the third auxiliary fastener (11), and the splayed needle seats (12) are provided on both sides of the third auxiliary fastener (11); each of the splayed needle seat (12) is rectangular bended, a third fixing hole (12-1) is provided on an upper end of the splayed needle seat (12), a semicircle slot (12-2) is provided on an upper middle of the splayed needle seat (12), an oval-shaped needle hole (12-3) is provided on a lower end of the splayed needle seat (12), screw holes (11-2) at both sides of the third auxiliary fastener (11) are connected and fixed with third fixing holes (12-1) by grub screws (8-1), the auxiliary fixing needles (13) are provided in the oval-shaped needle hole (12-3), the reinforcing nuts (7) are provided on the screw threads of each of the auxiliary fixing needles (13), and the reinforcing nuts (7) are fixed up and down to the oval-shaped needle hole.

12. The line-shaped paw-type patella external fixator according to claim 11, wherein the splayed needle seat (12) is divided into two pieces, and the two pieces are mounted on both sides of the third auxiliary fastener (11) by the third fixing hole (12-1); or the splayed needle seat (12) is an integrated splayed needle seat (12B), and the integrated splayed needle seat (12B) is mounted on the bottom or top of the third auxiliary fastener (11) by a forth fixing hole (12B-1).

* * * * *